(12) United States Patent
Watts et al.

(10) Patent No.: US 7,279,082 B2
(45) Date of Patent: Oct. 9, 2007

(54) METHOD OF REACTING CARBOXYLIC ACIDS

(75) Inventors: Paul Watts, Victoria Dock (GB); Stephen John Haswell, Cottingham (GB)

(73) Assignee: The University of Hull, Hull (GB)

( * ) Notice: Subject to any disclaimer, the term of this patent is extended or adjusted under 35 U.S.C. 154(b) by 597 days.

(21) Appl. No.: 10/659,738

(22) Filed: Sep. 11, 2003

(65) Prior Publication Data

US 2004/0079630 A1 Apr. 29, 2004

(30) Foreign Application Priority Data

Sep. 12, 2002 (GB) ................... 0221207.4

(51) Int. Cl.
*B01D 57/02* (2006.01)
(52) U.S. Cl. ...................... 204/450; 204/451
(58) Field of Classification Search ............ 205/413, 205/415; 204/450, 451, 600, 601; 422/131
See application file for complete search history.

(56) References Cited

U.S. PATENT DOCUMENTS

| 3,652,430 | A | | 3/1972 | Beck et al. |
| 4,006,065 | A | * | 2/1977 | Meresz et al. ............. 205/462 |
| 5,468,352 | A | | 11/1995 | Jager et al. |
| 6,238,543 | B1 | * | 5/2001 | Law et al. .................. 205/415 |
| 6,989,090 | B2 | * | 1/2006 | Haswell et al. .......... 205/793.5 |

FOREIGN PATENT DOCUMENTS

| DE | 1 443 445 | 11/1968 |
| DE | 1 802 865 | 9/1970 |

OTHER PUBLICATIONS

Haswell, S. J., "Development and Operating Characteristics of Micro Flow Injection Analysis Systems Based on Electroosmotic Flow", Analyst (Jan. 1997), vol. 122, pp. 1R-10R.*
Haswell, "Development and Operating Characteristics of Micro Flow Injection Analysis Systems Based on Electroosmotic Flow", Analyst, vol. 122, Jan. 1997, pp. 1R-10R.
Svadkovskaya et al., "Electrolytic Condensation of Carboxylic Acids", Russian Chemical Reviews, vol. 29. No. 3, Mar. 1960, pp. 161-180.
Yan et al., "A model for the Kolbe . . . reactor", Journal of Applied Electrochemistry, vol. 26, pp. 175-185 (1996), no month.
Ogumi et al., "Application of the solid polymer . . . Pt-SPE", Electrochimica Acta, vol. 28, pp. 1687-1693 (1983), no month.

* cited by examiner

*Primary Examiner*—Edna Wong
(74) *Attorney, Agent, or Firm*—B. Aaron Schulman; Stites & Harbison

(57) ABSTRACT

A carboxylic acid molecule (R COOH) is subjected to an electric field in a micro-reactor. The molecule decarboxyles to form a radical (R•). Two radicals (R•) can dimerise to form the product (R—R). It is believed that the reaction occurs away from the electrodes used to apply the electric field (but may also occur at the electrode surfaces).

27 Claims, 2 Drawing Sheets

METHOD OF REACTING CARBOXYLIC ACIDS

FIELD OF THE INVENTION

The invention relates to a method of reacting carboxylic acids.

SUMMARY OF THE INVENTION

In accordance with a first aspect of the invention, there is provided a method of reacting carboxylic acids comprising, using electrodes to apply an electrical voltage between opposite ends of a channel containing a liquid, providing first and second carboxylic acid molecules, each carboxylic acid molecule having a carbon atom $\alpha$ to a carboxylic acid group, the electrical voltage causing the carboxylic acid molecules to react together with the loss of the carboxylic acid groups and the formation of a product molecule in which a bond links the $\alpha$ carbon atoms together, the reaction taking place in the liquid in the channel and spaced from the electrodes.

In accordance with a second aspect of the invention, there is provided a method of reacting carboxylic acids comprising, providing first and second carboxylic acid molecules in a liquid in a channel, each carboxylic acid molecule having a carbon atom $\alpha$ to a carboxylic acid group, applying an electrical voltage to cause electro-osmotic movement of the liquid along the channel, the electrical voltage causing the carboxylic acid molecules to react together in the channel with the loss of the carboxylic acid groups and the formation of a product molecule in which a bond links the $\alpha$ carbon atoms together.

The methods of the current invention are useful in the chemical synthesis of a large number of products.

BRIEF DESCRIPTION OF THE INVENTION

The following is a more detailed description of examples of the invention, reference being made to the appended drawings in which.

DETAILED DESCRIPTION

The present invention is described with reference to the following non-limiting example

EXAMPLE 1

Figure 2:
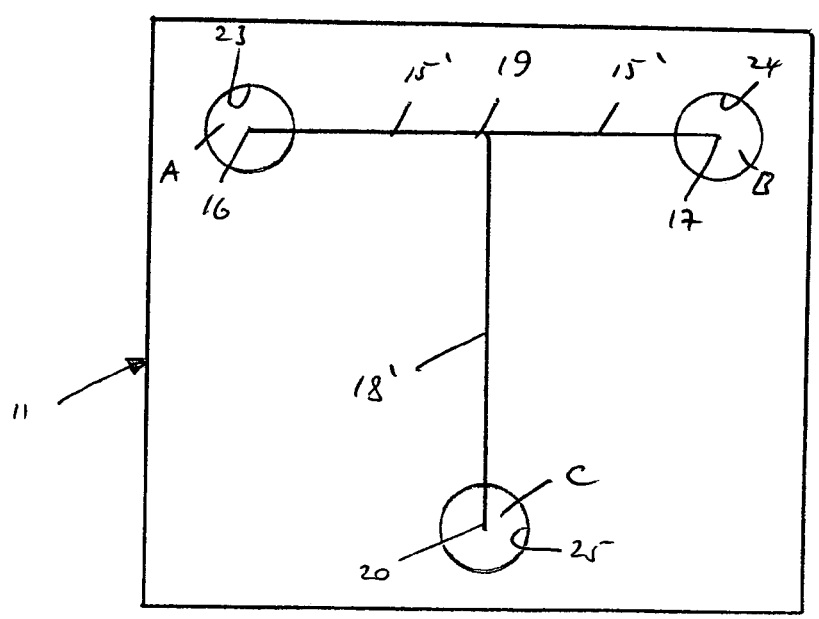
FIG. 2 is a schematic plan view from above of the assembled micro-reactor.
Figure 3:
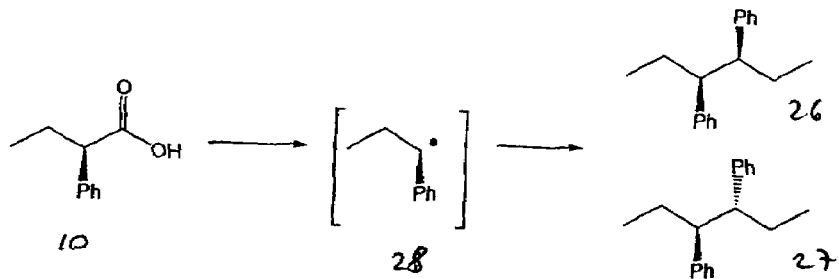
FIG. 3 is a reaction scheme showing the reaction of R-phenylbutyric acid to form stereoisomeric products.

In this example, R-phenylbutyric acid 10 is reacted as shown in FIG. 3, and as described in detail below. The reaction can be performed in the micro-reactor 11 shown in FIG. 2.

Figure 1:
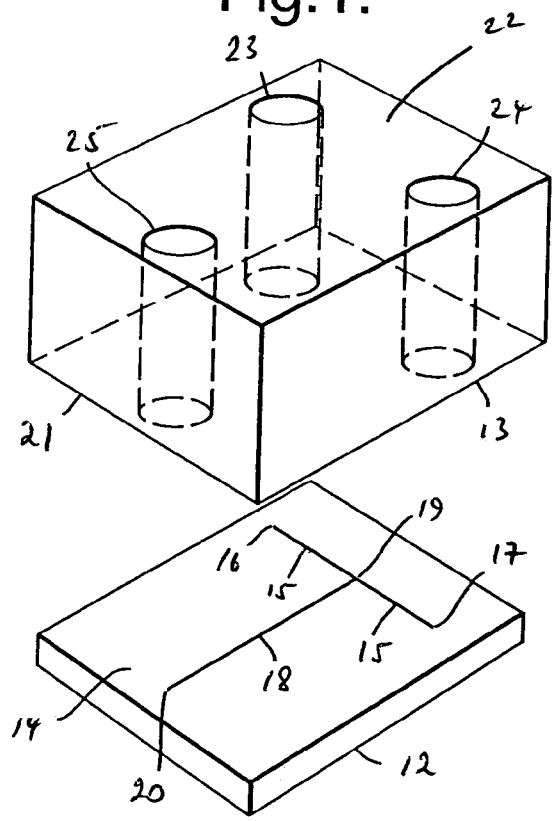
FIG. 1 is a schematic, perspective view of two blocks used to form a micro-reactor.

As shown in FIG. 1, the micro-reactor 11 is formed from a lower block 12 and an upper block 13, both of borosilicate glass. The lower block 12 has an upper surface 14 in which is formed a first groove 15 having a first end 16 and a second end 17. A second groove 18 is also formed in the upper surface 14 of the lower block 12. The second groove 18 extends perpendicularly to the first groove 15, from the mid-point 19 of the first groove 15 to an end 20 of the second groove 18. Each of the first and second grooves 15, 18 has a width of about 150 µm and a depth of about 30 µm. The grooves 15, 18 may be formed in any known manner, for example by etching.

The upper block 13 has a lower surface 21 and an opposite upper surface 22. First, second and third cylindrical holes 23, 24, 25 extend between the lower surface 21 and the upper surface 22 of the upper glass block 13.

To form the micro-reactor 11 shown in FIG. 2, the upper surface 14 of the lower glass block 12 is connected to the lower surface 21 of the upper glass block 13. The lower surface 21 of the upper glass block 13 closes the first groove 15 to form a first channel 15' of the micro-reactor 11 and also closes the second groove 18 to form a second channel 18' of the micro-reactor 11. The second channel 18' connects with the first channel 15' at the mid-point 19. When the upper surface 14 of the lower block 12 is connected to the lower surface 21 of the upper block 13, the first cylindrical hole 23 lies over the first end 16 of the first groove 15 and forms a first reservoir A, the second cylindrical hole 24 lies over the second end 17 of the first groove 15 and forms a second reservoir B, and the third cylindrical hole 25 lies over the end 20 of the second groove 18 and forms a third reservoir C. Hence, the first and second reservoirs A, B communicate with the first channel 15' and the third reservoir C communicates with the second channel 18'.

Each of the first channel 15' and the second channel 18' also has a width of about 150 µm and depth of about 30 µm.

In forming the micro-reactor 11, the upper surface 14 of the lower glass block 12 and the lower surface 21 of the upper glass block 13 may be connected in any known way, for example by thermal bonding.

The micro-reactor 11 is prepared for use by filling the first and second channels 15', 18' with dimethylformamide. This can be done, for example, by filling the first reservoir A with dimethylformamide and by applying a positive pressure to the first reservoir A so as to push the dimethylformamide through the first and second channels 15', 18'. Once the first and second channels 15', 18' have been filled with dimethylformamide, excess dimethylformamide is removed from the first, second and third reservoirs A, B, C.

A solution of 0.1 M R-phenylbutyric acid in dimethylformamide is then added to the first reservoir A. Dimethylformamide alone is added to the second reservoir B and to the third reservoir C. Respective platinum electrodes (not shown) are then placed in the first reservoir A and in the third reservoir C, so that the electrodes contact the respective liquids in the reservoirs. Then, while the electrode in the third reservoir C is maintained as a ground electrode, a voltage of from +700 to +1,000 V is applied to the electrode in the first reservoir A. The distance between the first and third reservoirs A, C, that is to say the distance along the first channel 15' from the first reservoir A to the mid-point 19 plus the distance from the mid-point 19 along the second channel 18' to the third reservoir C, is 3 cm. Accordingly, the voltage range of +700 to +1,000 V corresponds to an electrical field strength of about 230 to about 330 V/cm. Field strengths in this range have been found to be suitable for the reaction discussed below. The reaction discussed below was found not to occur at field strengths of less than about 230 V/cm in the micro-reactor described above.

The application of the voltage causes the R-phenylbutyric acid solution to move from the first reservoir A through the first channel 15' to the mid-point 19 and then through the second channel 18' to the third reservoir C. This movement is due to electro-osmosis caused by the electrical voltage. During this process, the R-phenylbutyric acid 10 is consumed to form the stereoisomeric products 26, 27 shown in FIG. 3. Without limiting the invention to any particular reaction mechanism, it is thought that the application of the electrical voltage causes each molecule of R-phenylbutyric acid 10 to de-carboxylate so as to form a respective molecule of the radical 28 shown in FIG. 3. De-carboxylation gives rise to $CO_2$. As shown in FIG. 3, the un-paired electron of each radical 28 is thought to be located on the carbon atom that was previously α to the carboxylic acid group of the R-phenylbutyric acid molecule 10 from which the radical 28 was formed. It is thought that two of these radicals 28 then dimerise with the formation of a carbon-carbon bond between the two a carbon atoms (i.e. the two carbon atoms that were previously α to the carboxylic acid groups of the R-phenylbutyric acid molecules). As seen in FIG. 3, the carbon atoms of the radicals 28 on which the free electrons are located are prochiral, and this explains the observed stereoisomeric nature of the product.

It is believed that the reaction shown in FIG. 3 takes place in the first and second channels 15', 18'. It is postulated that the redox processes may be induced inside the channels 15',18' due to a combination of electric field strength (i.e. $Vcm^{-1}$ applied) and polarization of solution based charge carrying species associated with the formation of the electrical double layer (that is involved in electro-osmotic flow) at the channel surface. The reaction may also take place (although not exclusively) at the surfaces of the electrodes.

Figure 4:
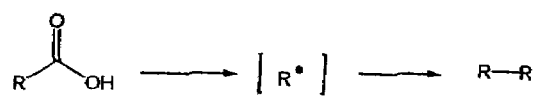
FIG. 4 is a reaction scheme showing reaction of a generic carboxylic acid.

The reaction can be performed with any carboxylic acid which has a carbon atom α to the carboxylic acid group. This is shown generically in FIG. 4. As represented in FIG. 4, two molecules of the carboxylic acid de-carboxylate to form two radicals, with the un-paired electrons being located on the carbon atoms that were previously α to the carboxylic acid groups. The two radicals then react with the formation of a bond between the carbon atoms that were previously α to the carboxylic acid groups. Although not shown in FIG. 4, the carboxylic acid groups give rise to carbon dioxide.

The fact that, in the system described above, the reaction of R-phenylbutyric acid did not occur at electric field strengths of less than about 230 V/cm means that the reaction can be controlled (turned on or off) by adjusting the voltage above or below this threshold. Similar electrical field thresholds may apply to other carboxylic acid reactions and/or other systems. These may not be at the same value (230 V/cm), but can be readily determined by simple experimentation.

EXAMPLE 2

Figure 5:
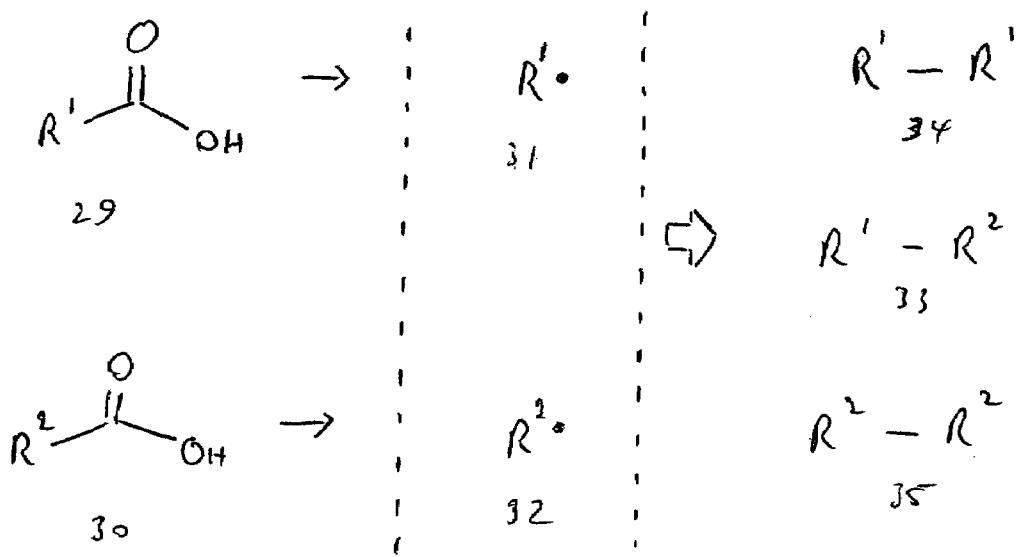
FIG. 5 shows the reaction of two different carboxylic acids to form three products.

In this example, first and second different carboxylic acids 29, 30 are reacted together, as shown schematically in FIG. 5, in the micro-reactor 11 described above in Example 1. Each of the two carboxylic acids 29, 30 that are reacted together has a carbon atom α to the carboxylic acid group.

Firstly, the first and second channels 15', 18' of the micro-reactor 11 are filed with dimethylformamide, as discussed above.

A 0.1 M solution of the first carboxylic acid 29 ($R^1COOH$), in dimethylformamide, is then added to the first reservoir A. A 0.1M solution of the second carboxylic acid 30 ($R^2COOH$), in dimethylformamide, is added to the second reservoir B. The solvent dimethylformamide is added to the third reservoir C. Respective platinum electrodes (not shown) are then placed in the first, second and third reservoirs A, B, C. While maintaining the electrode in the third reservoir C as the ground electrode, positive electrical voltages are applied to the electrodes in the first and second reservoirs A, B. Typically, respective voltages in the range of 100 to 2000 V, preferably 500 to 1000V, are applied to each of these electrodes.

The application of the voltages causes the solution of the first carboxylic acid 29 ($R^1COOH$) to move from the first reservoir A along the first channel 15' to the mid-point 19 and then along the second channel 18' towards the third reservoir C. Similarly, the application of the voltages causes the second carboxylic acid 30 ($R^2COOH$) to move from the second reservoir B along the first channel 15' to the mid-point 19 and then along the second channel 18' towards the third reservoir C. The movement of both of the solutions is caused by electro-osmosis. As will be evident from FIG. 2, the first carboxylic acid 29 ($R^1COOH$) and the second carboxylic acid 30 ($R^2COOH$) meet at the mid-point 19 and mix as the solutions progress along the second channel 18'.

It is believed that the application of the electrical voltages causes the first and second carboxylic acids 29, 30 to de-carboxylate and to form corresponding first and second radicals 31,32. Hence, as shown in FIG. 5, a molecule of the first carboxylic acid 29 ($R^1COOH$) forms a molecule of a first radical 31 ($R^1\bullet$) in which the un-paired electron is located on the carbon atom that was previously α to the carboxylic acid group. De-carboxylation of a molecule of the second carboxylic acid 30 ($R^2COOH$) gives rise to a molecule of a second radical 32 ($R^2\bullet$) in which the un-paired electron is also located on the carbon atom that was previously α to the carboxylic acid group. De-carboxylation gives rise to carbon dioxide. In the second channel 18', molecules of the first radical 31 ($R^1\bullet$) and molecules of the second radical 32 ($R^2\bullet$) exist together. Accordingly, a molecule of the first radical 31 ($R^1\bullet$) may react with a molecule of the second radical 32 ($R^2\bullet$) to form a molecule of a first product 33 ($R^1$—$R^2$) in which there is a carbon-carbon bond between the carbon atom that was previously α to the carboxylic acid group of the first carboxylic acid 29 ($R^1COOH$) and the carbon atom that was previous α to the carboxylic acid group of the second carboxylic acid 30 ($R^2COOH$). In a similar manner, two molecules of the first radical 31 ($R^1\bullet$) may dimerise to form a molecule of a second product 34 ($R^1$—$R^1$), and two molecules of the second radical 32 ($R^2\bullet$) may dimerise to form a molecule of a third product 35 ($R^2$—$R^2$). As for the first product 33 ($R^1$—$R^2$), the second product 34 ($R^1$—$R^1$) and the third product 35 ($R^2$—$R^2$) also have carbon-carbon bonds between the carbon atoms that were previously α to the carboxylic acid groups.

In the portion of the first channel 15' leading from the first reservoir A to the mid-point 19 the first radical 31 ($R^1\bullet$) may be formed and may dimerise to form the second product ($R^1$—$R^1$). In the portion of the first channel 15' extending between the second reservoir B and the mid-point 19, the second radical 32 ($R^2\bullet$) may be formed and may dimerise to form the third product 35 ($R^2$—$R^2$). However the first and second radicals 31, 32 ($R^1\bullet$ and $R^2\bullet$) do not exist together in these portions and so the first product 33 ($R^1$—$R^2$) is not formed in these portions.

The first and second carboxylic acids 29,30 ($R^1COOH$ and $R^2COOH$) can be any different carboxylic acids that have a carbon atom α to a carboxylic acid group.

It will be appreciated that the methods discussed above may be modified while remaining within the scope of the claims.

Firstly, the method of the current invention may be performed in micro-reactors having any number of channels. Where there are a plurality of channels, the channels may be interconnected in any desired configuration. The carboxylic acid reactions of the current invention may be combined with other reactions, in the same micro-reactor.

The micro-reactor 11 of Examples 1 and 2 above need not be made of borosilicate glass. Where electro-osmotic flow is required, micro-reactors are generally made from materials that have negatively charged surfaces. Other suitable materials are silica and quartz. A more detailed description of electro-osmosis, and the requirements for electro-osmotic flow is given in the review by S J Haswell entitled "Development and Operating Characteristics of Miro Flow Injection Analysis Systems Based on Electro-osmotic Flow" in Analyst, January 1997, Vol. 122(1R-10R). This document is incorporated herein by reference.

In Examples 1 and 2 above, where electro-osmosis takes place, the solvent dimethylformamide may be replaced by any solvent capable of supporting electro-osmotic flow. As more thoroughly discussed in the review by S J Haswell, a solvent suitable for electro-osmosis should either disassociate to some extent to generate positive ions (that counter the negative surface charges lining the channels of the micro-reactor), or should form dipoles having the same effect. Other suitable solvents include tetrahydrofuran, methanol, dimethyl sulfoxide, ethanol, and acetonitrile.

It will be appreciated that the channel of the current invention may be a portion of a larger channel. The channel may be considered to have "ends", which delineate it from the rest of the larger channel, but which need not be marked by any change in channel configuration. Hence, the channel can be a portion of a larger channel that has a constant cross-sectional configuration along its whole length.

Throughout this specification, the terms carboxylic acid and carboxylic acid molecule cover both carboxylic acid molecules and also molecules of the corresponding carboxylate anions (i.e. RC00$^-$).

The cross-sectional configuration and dimensions of the channel of the current invention may vary. In general, the channel preferably has a maximum cross-sectional dimension in the range of 10 to 400 μm. More preferably, the maximum cross-sectional dimension is in the range of 100 to 200 μm.

In the Examples given above, the carboxylic acids are reacted using 0.1 M solutions. Other concentrations may be used. Preferably the carboxylic acids will be used at concentrations in the range of from 0.01 to 5.0 M, and more preferably from 0.1 to 0.5M.

We claim:

1. A method of reacting carboxylic acids comprising, using electrodes to apply an electrical voltage between opposite ends of a channel containing a liquid, providing first and second carboxylic acid molecules, each carboxylic acid molecule having a carbon atom a to a carboxylic acid group, the electrical voltage causing said carboxylic acid molecules to react together with the loss of said carboxylic acid groups and the formation of a product molecule in which a bond links said a carbon atoms together, said reaction taking place in the liquid in the channel and spaced from the electrodes.

2. A method according to claim 1, wherein the electrical voltage causes electro-osmotic movement of the liquid along the channel.

3. A method according to claim 1, wherein the channel has a maximum cross-sectional dimension in the range of from 10 to 400 pm.

4. A method according to claim 3, wherein the maximum cross-sectional dimension is in the range from 100 to 200 pm.

5. A method according to claim 1, wherein the first and second molecules are of the same carboxylic acid.

6. A method according to claim 1, wherein the first and second molecules are of different carboxylic acids.

7. A method according to claim 1, wherein said reaction is repeated for a plurality of pairs of carboxylic acid molecules, so that each pair produces a respective product molecule, the product molecules comprising stereoisomeric forms.

8. A method according to claim 1, wherein the channel has a length and the field strength of the electric voltage in the channel is at least about 230 V/cm of said length.

9. A method according to claim 8, wherein the field strength is in the range from about 230 to about 330 V/cm of the length.

10. A method according to claim 1, wherein the channel is one of a plurality of interconnecting channels.

11. A method according to claim 1, wherein the channel is formed in an apparatus formed from two members, one of the members being provided with a groove, the groove corresponding to the channel, the other one of the members having a surface that closes the groove to form the channel.

12. A method according to claim 1, wherein the liquid is selected from the group consisting of dimethylformamide, tetrahydrofuran, methanol, dimethyl sulfoxide, ethanol and acetonitrile.

13. A method according to claim 1, wherein the channel is formed in a body formed from a material selected from the group consisting of glass, silica and quartz.

14. A method according to claim 13, wherein the glass material is borosilicate glass.

15. A method of reacting carboxylic acids comprising, providing first and second carboxylic acid molecules in a liquid in a channel, each carboxylic acid molecule having a carbon atom α to a carboxylic acid group, applying an electrical voltage to cause electro-osmotic movement of the liquid along the channel, the electrical voltage causing said carboxylic acid molecules to react together in the channel with the loss of said carboxylic acid groups and the formation of a product molecule in which a bond links said α carbon atoms together.

16. A method according to claim 15, wherein the channel has a maximum cross-sectional dimension in the range of from 10 to 400 μm.

17. A method according to claim 16, wherein the maximum cross-sectional dimension is in the range from 100 to 200 μm.

18. A method according to claim 15, wherein the first and second molecules are of the same carboxylic acid.

19. A method according to claim 15, wherein the first and second molecules are of different carboxylic acids.

20. A method according to claim 15, wherein said reaction is repeated for a plurality of pairs of carboxylic acid molecules, so that each pair produces a respective product molecule, the product molecules comprising stereoisomeric forms.

21. A method according to claim 15, wherein the channel has a length and the field strength of the electric voltage in the channel is at least about 230 V/cm of said length.

22. A method according to claim 21, wherein the field strength is in the range from about 230 to about 330 V/cm of the length.

23. A method according to claim 15, wherein the channel is one of a plurality of interconnecting channels.

24. A method according to claim 15, wherein the channel is formed in an apparatus formed from two members, one of the members being provided with a groove, the groove corresponding to the channel, the other one of the members having a surface that closes the groove to form the channel.

25. A method according to claim 15, wherein the liquid is selected from the group consisting of dimethylformamide, tetrahydrofuran, methanol, dimethyl sulfoxide, ethanol and acetonitrile.

26. A method according to claim 15, wherein the channel is formed in a body formed from a material selected from the group consisting of glass, silica and quartz.

27. A method according to claim 26, wherein the glass material is borosilicate glass.

* * * * *

UNITED STATES PATENT AND TRADEMARK OFFICE
CERTIFICATE OF CORRECTION

PATENT NO. : 7,279,082 B2  Page 1 of 1
APPLICATION NO. : 10/659738
DATED : October 9, 2007
INVENTOR(S) : Watts et al.

It is certified that error appears in the above-identified patent and that said Letters Patent is hereby corrected as shown below:

On the Title page item (57) Abstract, line 2, please change "decarboxyles" to --decarboxylates--

Column 3, line 17: change "two a carbon atoms" to --two α carbon atoms--.

Column 5, line 55 (claim 1): change "a carbon atom a to a carboxylic acid" to --a carbon atom α to a carboxylic acid--.

Column 5, line 59: change "a bond links said a carbon atoms together" to --a bond links said α carbon atoms together--.

Column 5, line 67 (claim 3): change "10 to 400 pm" to --10 to 400 μm--

Column 6, line 3 (claim 4): change "pm" to --μm--

Signed and Sealed this

Ninth Day of September, 2008

JON W. DUDAS
*Director of the United States Patent and Trademark Office*